(12) United States Patent
Andre et al.

(10) Patent No.: US 10,101,571 B2
(45) Date of Patent: Oct. 16, 2018

(54) PERFUSION ASSESSMENT MULTI-MODALITY OPTICAL MEDICAL DEVICE

(71) Applicant: Novadaq Technologies ULC, Burnaby (CA)

(72) Inventors: Marc Andre, Spiegel b. Bern (CH); Michael Friedrich, Bern (CH)

(73) Assignee: NOVADAQ TECHNOLOGIES ULC, Burnaby (CA)

( * ) Notice: Subject to any disclaimer, the term of this patent is extended or adjusted under 35 U.S.C. 154(b) by 242 days.

(21) Appl. No.: 14/413,106

(22) PCT Filed: Jul. 5, 2013

(86) PCT No.: PCT/IB2013/055517
§ 371 (c)(1),
(2) Date: Jan. 6, 2015

(87) PCT Pub. No.: WO2014/009859
PCT Pub. Date: Jan. 16, 2014

(65) Prior Publication Data
US 2015/0198797 A1  Jul. 16, 2015

(30) Foreign Application Priority Data

Jul. 10, 2012 (WO) .................. PCT/IB2012/053524

(51) Int. Cl.
*G02B 21/36* (2006.01)
*G02B 21/16* (2006.01)
(Continued)

(52) U.S. Cl.
CPC .......... *G02B 21/365* (2013.01); *A61B 5/0035* (2013.01); *A61B 5/0261* (2013.01);
(Continued)

(58) Field of Classification Search
CPC ... A61B 5/0035; A61B 5/0261; A61B 5/7425; A61B 90/361; G02B 21/16; G02B 21/365; G02B 2207/113
See application file for complete search history.

(56) References Cited

U.S. PATENT DOCUMENTS 4,862,894 A  9/1989 Fujii
5,267,016 A  11/1993 Meinzer et al.
(Continued)

FOREIGN PATENT DOCUMENTS

CN         101926644 A       12/2010
DE    10 2008 017 390 A1    10/2009
(Continued)

OTHER PUBLICATIONS

Briers, J.D. (Nov. 2001). "Laser Doppler, Speckle and Related Techniques for Blood Perfusion Mapping and Imaging," *Physiol. Meas.* 22(4):R35-R66.
(Continued)

*Primary Examiner* — Md N Haque
(74) *Attorney, Agent, or Firm* — Morrison & Foerster LLP

(57) ABSTRACT

A perfusion assessment multi-modality optical medical device comprising
- a white light image sensor (320) and optical system configured to image a body area of interest (130, 340),
  a coherent light source (330) for illuminating said body area of interest with wavelength of 760-810 nm,
  an optical coherence imaging (OCI) image sensor (310) detecting the fluctuations of the backscattered light (302) near the illumination wavelength from at least part of said illuminated body area of interest (340),
  a fluorescence image sensor (315) to detect the fluorescence signal at higher wavelength than the illumination wavelength from at least part of said illuminated body area of interest (340), (Continued)

Figure 1:
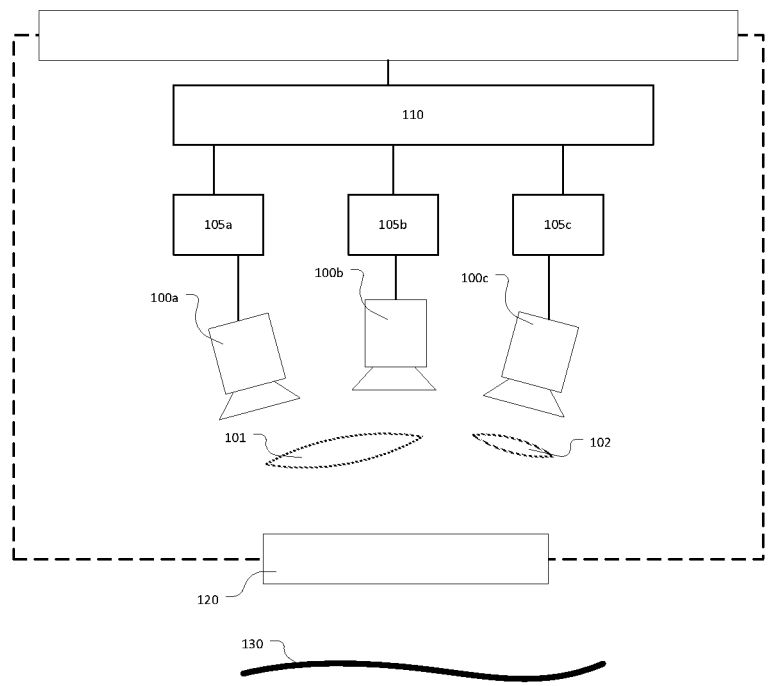

a screen (115, 210) to show the results from the modalities, all previous items being included in a single movable unit (200) which furthermore comprises a processing unit (105, 110) to calculate perfusion map from the OCI image sensor (310) using LDI or LSI algorithms, wherein said white light image sensor (320), said OCI image sensor (310) and said fluorescence image sensor (315), at least partially, use a common optical path (610).

16 Claims, 6 Drawing Sheets

(51) Int. Cl.
  *A61B 5/00* (2006.01)
  *A61B 5/026* (2006.01)
  *A61B 90/00* (2016.01)

(52) U.S. Cl.
  CPC .......... *A61B 5/7425* (2013.01); *A61B 90/361* (2016.02); *G02B 21/16* (2013.01); *G02B 2207/113* (2013.01)

(56) References Cited

U.S. PATENT DOCUMENTS

| | | | |
|---|---|---|---|
| 5,685,313 A | 11/1997 | Mayevsky | |
| 6,045,511 A | 4/2000 | Ott et al. | |
| 6,073,041 A | 6/2000 | Hu et al. | |
| 6,178,340 B1 | 1/2001 | Svetliza | |
| 6,263,227 B1 | 7/2001 | Boggett et al. | |
| 6,485,413 B1* | 11/2002 | Boppart | A61B 1/00096 356/450 |
| 6,728,561 B2 | 4/2004 | Smith et al. | |
| 6,970,729 B2 | 11/2005 | Hartmann | |
| 7,113,817 B1 | 9/2006 | Winchester, Jr. et al. | |
| 7,123,363 B2 | 10/2006 | Puttappa et al. | |
| 7,231,243 B2 | 6/2007 | Tearney et al. | |
| 7,483,062 B2 | 1/2009 | Allman et al. | |
| 7,519,212 B2 | 4/2009 | Brady et al. | |
| 8,298,521 B2 | 10/2012 | Schwartz et al. | |
| 8,480,579 B2 | 7/2013 | Serov et al. | |
| 9,066,686 B2 | 6/2015 | Lasser et al. | |
| 9,757,039 B2 | 9/2017 | Lasser et al. | |
| 2002/0052551 A1 | 5/2002 | Sinclair et al. | |
| 2002/0082480 A1* | 6/2002 | Riff | G06F 19/3418 600/300 |
| 2003/0023153 A1 | 1/2003 | Izatt et al. | |
| 2003/0118649 A1* | 6/2003 | Gao | A61K 9/0024 424/471 |
| 2003/0137669 A1 | 7/2003 | Rollins et al. | |
| 2004/0034294 A1 | 2/2004 | Kimball et al. | |
| 2004/0176701 A1 | 9/2004 | Fujii | |
| 2004/0225222 A1 | 11/2004 | Zeng et al. | |
| 2005/0187477 A1 | 8/2005 | Serov et al. | |
| 2005/0197559 A1 | 9/2005 | Boese et al. | |
| 2005/0206583 A1 | 9/2005 | Lemelson et al. | |
| 2005/0288565 A1 | 12/2005 | Kerr | |
| 2006/0064024 A1* | 3/2006 | Schnall | A61B 5/02007 600/500 |
| 2006/0111620 A1* | 5/2006 | Squilla | A61B 5/00 600/300 |
| 2007/0016079 A1 | 1/2007 | Freeman et al. | |
| 2007/0100245 A1 | 5/2007 | Kashima | |
| 2007/0139613 A1 | 6/2007 | Tanifuji et al. | |
| 2007/0188707 A1 | 8/2007 | Nanjo | |
| 2007/0225606 A1 | 9/2007 | Naghavi et al. | |
| 2007/0239034 A1* | 10/2007 | Knoche | A61B 5/0059 600/476 |
| 2007/0291277 A1 | 12/2007 | Everett et al. | |
| 2008/0017787 A1* | 1/2008 | Okawa | A61B 1/0615 250/226 |
| 2008/0021329 A1 | 1/2008 | Wood et al. | |
| 2008/0100612 A1 | 5/2008 | Dastmalchi et al. | |
| 2008/0241199 A1 | 10/2008 | Silverman | |
| 2008/0294047 A1 | 11/2008 | Kodama et al. | |
| 2009/0054788 A1 | 2/2009 | Hauger et al. | |
| 2009/0130650 A1* | 5/2009 | Tan | C12N 15/115 435/5 |
| 2009/0192358 A1* | 7/2009 | Jaffer | A61B 5/0066 600/182 |
| 2010/0049055 A1 | 2/2010 | Freudenberg et al. | |
| 2010/0099992 A1 | 4/2010 | Holschneider et al. | |
| 2010/0113940 A1* | 5/2010 | Sen | A61B 5/0062 600/476 |
| 2010/0191541 A1 | 7/2010 | Prokoski | |
| 2011/0013002 A1 | 1/2011 | Thompson et al. | |
| 2011/0090325 A1* | 4/2011 | Hauger | A61B 5/0261 348/77 |
| 2011/0099031 A1* | 4/2011 | Nair | G06F 19/3418 705/3 |
| 2011/0169978 A1* | 7/2011 | Lasser | A61B 3/1233 348/222.1 |
| 2012/0071765 A1 | 3/2012 | Chinnock | |
| 2012/0078113 A1 | 3/2012 | Whitestone et al. | |
| 2012/0277559 A1 | 11/2012 | Kohl-Bareis et al. | |
| 2013/0172735 A1 | 7/2013 | Andre et al. | |
| 2013/0223705 A1 | 8/2013 | Ferguson, Jr. et al. | |
| 2013/0296715 A1 | 11/2013 | Lasser et al. | |
| 2015/0080742 A1 | 3/2015 | Andre et al. | |
| 2016/0328848 A1 | 11/2016 | Andre et al. | |
| 2016/0367145 A1 | 12/2016 | Lasser et al. | |
| 2018/0098702 A1 | 4/2018 | Lasser et al. | |

FOREIGN PATENT DOCUMENTS

| | | |
|---|---|---|
| EP | 0763998 A1 | 3/1997 |
| EP | 1 210 910 A1 | 6/2002 |
| EP | 1241979 A1 | 9/2002 |
| EP | 1 982 645 A1 | 10/2008 |
| JP | S-63-214238 A | 9/1988 |
| JP | H10-508763 A | 9/1998 |
| JP | H11-1427848 A | 5/1999 |
| JP | 2003-516795 A | 5/2003 |
| JP | 2003-527700 A | 9/2003 |
| JP | 2004-267308 A | 9/2004 |
| JP | 2005-515818 A | 6/2005 |
| JP | 2005-532393 A | 10/2005 |
| JP | 2006-180926 A | 7/2006 |
| JP | 2007-315827 A | 12/2007 |
| JP | 2008-142355 A | 6/2008 |
| JP | 2008-541891 A | 11/2008 |
| JP | 2008-289870 A | 12/2008 |
| JP | 2010-532699 A | 10/2010 |
| JP | 2011-027895 A | 2/2011 |
| JP | 2012-113191 A | 6/2012 |
| WO | WO-1995/32664 A1 | 12/1995 |
| WO | WO-2001/43628 A1 | 6/2001 |
| WO | WO-03/063677 A1 | 8/2003 |
| WO | WO-2005/099572 A1 | 10/2005 |
| WO | WO-2005/099582 A1 | 10/2005 |
| WO | WO-2006/111836 A1 | 10/2006 |
| WO | WO-2006/111909 A1 | 10/2006 |
| WO | WO-2006/121984 A2 | 11/2006 |
| WO | WO-2006/121984 A3 | 11/2006 |
| WO | WO-2007/148073 A1 | 12/2007 |
| WO | WO-2009/028136 A1 | 3/2009 |
| WO | WO 2010/004365 A1 | 1/2010 |
| WO | WO-2011/084528 A1 | 7/2011 |
| WO | WO 2011/117779 A2 | 9/2011 |
| WO | WO-2013/160861 A1 | 10/2013 |
| WO | WO-2014/009859 A2 | 1/2014 |
| WO | WO-2014/009859 A3 | 1/2014 |

OTHER PUBLICATIONS

Dyck, R.H. et al. (1968). "Integrated Arrays of Silicon Photodetectors for Image Sensing," *IEEE Transactions on Electron Devices* 15(4):196-202.

(56) References Cited

OTHER PUBLICATIONS

Georg, M. et al. (Jun. 2002). "Flickering Light Increases Retinal Blood Flow," *Database Biosis [Online] Biosciences Information Service* 22(3):336-343, two pages.
Jones, P.B. et al. (Jul.-Aug. 2008) "Simultaneous Multispectral Reflectance Imaging and Laser Speckle Flowmetry of Cerebral Blood Flow and Oxygen Metabolism in Focal Celebral Ischemia," *J. Biomed Opt.* 13(4):04407, twenty three pages.
Jeong, K. et al. (Feb. 20, 2006). "Functional Optical Coherence Imaging of Tumor Response to a Metabolic Electron Transport Inhibitor," *Proceedings of the SPIE* 6079(1):60790K-1-60790K-8.
Leutenegger, M. et al. (May 9, 2011). "Real-Time Full Field Laser Doppler Imaging," *Biomedical Optics Express* 2(6):1470-1477.
Schmeisser, E.T. et al. (May 2003). "Modification of the Heidelberg Retinal Flowmeter to Record Pattern and Flicker Induced Blood Flow Changes," *Documenta Ophthalmologica* 106(3):257-263.
Serov, A. et al. (Oct. 3, 2001). "Speckles in Laser Doppler Blood Flowmetry," *Proceedings of the SPIE* 4242:306-318.
Serov, A. (2002). "Novel Instruments for Remote and Direct-Contact Laser Doppler Perfusion Imaging and Monitoring," Ph.D. Thesis, University of Twente, 128 pages.
Canadian Office Action dated Nov. 10, 2016 for Canadian Patent Application No. 2,914,780 filed on Jul. 10, 2012, four pages.
Canadian Office Action dated Oct. 12, 2016 for Canadian Application No. 2,909,914 filed on Apr. 25, 2013, four pages.
European Communication pursuant to Article 94(3) EPC dated Nov. 25, 2016 for European Application No. 08789265.9, filed on Feb. 8, 2011, five pages.
European Office Action dated Aug. 19, 2008, for EP Application No. 06 744 526.2, filed on Apr. 20, 2006, three pages.
European Office Action dated Dec. 4, 2012, for EP Application No. 06 744 526.2, filed on Apr. 20, 2006, four pages.
European Office Action dated Jul. 1, 2010, for EP Application No. 06 744 526.2, filed on Apr. 20, 2006, five pages.
International Preliminary Report on Patentability (IPRP) (Chapter I) for PCT/IB2008/052787, dated Jan. 11, 2011.
International Search and Written Opinion dated Jul. 15, 2016 for PCT Application No. PCT/CA2016/050526, filed on May 6, 2016, eight pages.
International Search Report dated Aug. 14, 2006, for PCT Patent Application No. PCT/IB2006/000940, filed on Apr. 20, 2006, three pages.
International Search Report dated Aug. 14, 2006, for PCT Patent Application No. PCT/IB2006/051167, filed on Apr. 13, 2006, three pages.
International Search Report dated Mar. 24, 2009, for PCT Application No. PCT/IB2008/052787, filed on Jul. 10, 2008, five pages.
International Search Report dated Nov. 23, 2011, for PCT Application No. PCT/IB2011/051098, filed on Mar. 16, 2011, seven pages.
International Search Report dated Sep. 11, 2013, for PCT Application No. PCT/IB2013/053271, filed on Apr. 25, 2013, four pages.
Japanese Office Action dated Feb. 1, 2016, for Japanese Patent Application No. 2015-521112, filed Jul. 5, 2013, twelve pages.
Japanese Office Action dated Oct. 30, 2015, for Japanese Patent Application No. 2015-507652, filed on Apr. 25, 2013, seven pages.
U.S. Final Office Action dated Apr. 4, 2016, for U.S. Appl. No. 13/636,268, filed Mar. 4, 2013, thirteen pages.
U.S. Final Office Action dated Aug. 18, 2011, for U.S. Appl. No. 11/912,224, filed Oct. 22, 2007, five pages.
U.S. Final Office Action dated Aug. 23, 2013, for U.S. Appl. No. 13/057,593, filed Mar. 21, 2011, fourteen pages.
U.S. Final Office Action dated Dec. 16, 2016 for U.S. Appl. No. 13/935,947, filed Jul. 5, 2013, twenty three pages.
U.S. Final Office Action dated Feb. 20, 2015, for U.S. Appl. No. 13/636,268, filed Mar. 4, 2013, seventeen pages.
U.S. Final Office Action dated Nov. 29, 2012, for U.S. Appl. No. 11/912,224, filed Oct. 22, 2007, eight pages.
U.S. Final Office Action dated Oct. 6, 2015, for U.S. Appl. No. 13/935,947, filed Jul. 5, 2013, fifteen pages.
U.S. Final Office Action dated Sep. 26, 2016, for U.S. Appl. No. 13/636,268, filed Mar. 4, 2013, fifteen pages.
U.S. Non Final Office Action dated Jan. 13, 2017 for U.S. Appl. No. 14/397,290, filed Oct. 27, 2014, fifteen pages.
U.S. Non-Final Office Action dated Apr. 29, 2016, for U.S. Appl. No. 13/935,947, filed Jul. 5, 2013, twenty pages.
U.S. Non-Final Office Action dated Aug. 11, 2014, for U.S. Appl. No. 13/057,593, filed Mar. 21, 2011, nineteen pages.
U.S. Non-Final Office Action dated Dec. 17, 2012, for U.S. Appl. No. 13/057,593, filed Mar. 21, 2011, fourteen pages.
U.S. Non-Final Office Action dated Jan. 16, 2015, for U.S. Appl. No. 13/935,947, filed Jul. 5, 2013, seven pages.
U.S. Non-Final Office Action dated Mar. 14, 2012, for U.S. Appl. No. 11/912,224, filed Oct. 22, 2007, seven pages.
U.S. Non-Final Office Action dated Mar. 8, 2011, for U.S. Appl. No. 11/912,224, filed Oct. 22, 2007, nine pages.
U.S. Non-Final Office Action dated Nov. 3, 2015, for U.S. Appl. No. 13/636,268, filed Mar. 4, 2013, fourteen pages.
U.S. Non-Final Office Action dated Sep. 29, 2014, for U.S. Appl. No. 13/636,268, filed Mar. 4, 2013, ten pages.
U.S. Non-Final Office Action dated Feb. 1, 2017, for U.S. Appl. No. 14/753,997, filed Jun. 29, 2015, seven pages.
U.S. Notice of Allowance dated Feb. 27, 2015, for U.S. Appl. No. 13/057,593, filed Mar. 21, 2011, eight pages.
U.S. Notice of Allowance dated May 9, 2013, for U.S. Appl. No. 11/912,224, filed Oct. 22, 2007, six pages.
Written Opinion of the International Searching Authority dated Aug. 14, 2006, for PCT Patent Application No. PCT/IB2006/000940, filed on Apr. 20, 2006, seven pages.
Written Opinion of the International Searching Authority dated Aug. 14, 2006, for PCT Patent Application No. PCT/IB2006/051167, filed on Apr. 13, 2006, seven pages.
Written Opinion of the International Searching Authority dated Mar. 24, 2009, for PCT Application No. PCT/IB2008/052787, filed on Jul. 10, 2008, nine pages.
Written Opinion of the International Searching Authority dated Sep. 11, 2013, for PCT Application No. PCT/IB2013/053271, filed on Apr. 25, 2013, seven pages.
Written Opinion of the International Searching Authority dated Nov. 23, 2011, for PCT Application No. PCT/IB2011/051098, filed on Mar. 16, 2011, ten pages.
Written Opinion of the International Searching Authority dated Jan. 3, 2014, for PCT Application No. PCT/IB2013/055517, filed on Jul. 5, 2013, ten pages.
European Communication Pursuant to Rule 164(2)(b) and Article 94(3) EPC dated Jun. 20, 2017, for EP Application No. 11718157.8 , filed on Mar. 16, 2011, eight pages.
Japanese Office Action dated Jul. 7, 2017, for Japanese Application No. 2016-199363, filed on Oct. 7, 2016, eight pages.
U.S. Notice of Allowance dated May 5, 2017, for U.S. Appl. No. 14/753,997, filed Jun. 29, 2015, five pages.
U.S. Supplemental Notice of Allowability dated May 24, 2017, for U.S. Appl. No. 14/753,997, filed Jun. 29, 2015, three pages.
Golpayegani, G.N. et al. (May 16, 2008). "Laser Doppler and Laser Speckle Techniques for Blood flow Measurement," *2nd International Conference on Bioinformatics and Biomedical Engineering* pp. 1555-1560.
Hillman, E.M. (Sep.-Oct. 2007). "Optical Brain Imaging In Vivo: Techniques and Applications from Animal to Man," *J Biomed Opt.* 12(5):051402, total of 49 pages.
Canadian Notice of Allowance dated Sep. 22, 2017, for Canadian Patent Application No. 2,909,914, filed on Oct. 20, 2015, one page.
Canadian Notice of Allowance dated Oct. 27, 2017, for Canadian Patent Application No. 2,914,780, filed on Dec. 8, 2015, one page.
International Preliminary Report on Patentability (IPRP) (Chapter I) dated Nov. 16, 2017 for PCT Application No. PCT/CA2016/ 050526, filed on May 6, 2016, six pages.
U.S. Final Office Action dated Sep. 29, 2017 for U.S. Appl. No. 14/397,290, filed Oct. 27, 2014, nineteen pages.
U.S. Non Final Office Action dated Sep. 29, 2017 for U.S. Appl. No. 13/935,947, filed Jul. 5, 2013, twenty eight pages.
U.S. Non-Final Office Action dated Feb. 14, 2017, for U.S. Appl. No. 13/636,268, filed Mar. 4, 2013, thirteen pages.

(56) References Cited

OTHER PUBLICATIONS

U.S. Non-Final Office Action dated Dec. 14, 2017, for U.S. Appl. No. 15/148,959, filed May 6, 2016, twelve pages.
European Communication pursuant to Article 94(3) EPC dated Mar. 15, 2018 for European Application No. 11718157.8, filed on Mar. 16, 2011, four pages.
European Communication under Rule 71(3) EPC Intention to Grant dated Apr. 24, 2018 for EP Application No. 08789265.9, filed on Feb. 8, 2011, seven pages.
Japanese Notice of Allowance dated Jan. 12, 2018 for Japanese patent Application No. 2016-199363 filed on Oct. 7, 2016, six pages.
U.S. Final Office Action dated Apr. 25, 2018, for U.S. Appl. No. 13/935,947, filed Jul. 5, 2013, thirty three pages.
U.S. Non Final Office Action dated Apr. 18, 2018 for U.S. Appl. No. 14/397,290, filed Oct. 27, 2014, twenty three pages.
U.S. Non-Final Office Action dated Mar. 5, 2018, for U.S. Appl. No. 13/636,268, filed Mar. 4, 2013, seventeen pages.
Kalchenko, Vyacheslav et al. "Multi-modal Diagnostic Approach for Functional Imaging of Tumor Vascular Network and Blood Microcirculation," Dynamics and Fluctuations is Biomedical Photonics VIII, vol. 7898, No. 1, pp. 1-7 (Feb. 10, 2011).
Senarathna, Janaka et al. "Laser Speckle Contrast Imaging: Theory, Instrumentation, and Applications," IEEE Reviews in Biomedical Engineering, vol. 6, pp. 99-110 (Jan. 28, 2013).
Sun, Xiaoli et al. "Simultaneous Monitoring of Intracellular PH Changes and Hemodynamic Response During Cortical Spreading Depression by Fluorescence-Corrected Multimodal Optical Imaging," Neuroimage, vol. 57, No. 3, pp. 873-884 (May 14, 2011).
PCT International Search Report from counterpart Int'l App. No. PCT/IB2013/055517 (dated Jan. 3, 2014).

\* cited by examiner a)  b)  c)

PERFUSION ASSESSMENT MULTI-MODALITY OPTICAL MEDICAL DEVICE

FIELD OF INVENTION

The invention relates to perfusion assessment using medical imaging.

DEFINITIONS

Optical Coherent Imaging (OCI): A contactless and non-invasive medical imaging modality utilizing the physical properties, and in particular the coherence properties, of light to record, measure, visualize and/or assess physiological and non-physiological flow properties, and in particular blood flow properties, in a selected tissue and/or Body Area of Interest. OCI systems comprise of at least, but are not limited to: a coherent light source, a light acquisition unit, an image and data processing and device control unit, and means to visualize or otherwise represent the flow information. Specific implementations of OCI include, but are not limited to: Laser Doppler Imaging (LDI), Laser Doppler Spectroscopic Imaging (LDSI), Laser Speckle Imaging (LSI), Laser Speckle Contrast Analysis (LASCA), and Functional Optical Coherent Imaging (fOCI).

LSI/LASCA: LSI and LASCA are OCI technologies. The difference between LSI and LASCA is very small, thus in this document Laser Speckle Imaging (LSI) and Laser Speckle Contrast Analysis (LASCA) shall be synonyms.

Device means the multi-modality optical medical device.

Display and Screen shall be used as synonyms.

3D Screen: Any screen or display that facilitates the viewing of 3D or 3D-like images.

Device Head: The part of the device that contains the entry for the optical beam(s) and the screen in a single movable unit.

Optical Marker: Any feature the can be affixed to a body or device which has optical characteristics that facilitates its detection using an optical sensor. Often the orientation of the marker can be detected as well. Optical markers detected by a sensor system allow the identification of their position in the space.

Modality: Any detector system or mode of operation integrated into the Device. Examples are Laser Doppler Imaging, Fluorescence Imaging, Microscopy, or reviewing of pre-recorded image or meta-data of any type of origin linked to the Body Area of Interest.

Digital Microscope: A system comprising an optical system, an image sensor and a screen facilitating the magnification of an area and displaying it on the screen.

Map: A multi-dimensional (usually 2D) array of values. Often the values are mapped to an image by assigning a color to each value (i.e. by using a Colormap).

Colormap: Transformation of a value to a color. Such transformation is done using a table and/or algorithm. A Colormap is used to convert a Map of values to an image.

Working Distance: The distance between the optical system aperture of the Device Head and the Body Area of Interest.

Body Area of Interest: The area on the patient where the Device Head is pointed to and which us being imaged by any of the Modalities. The area can differ between Modalities (e.g. different size).

Microphone: A sensor that allows detection of sound waves.

ICG: Indocyanine green

ECG: Electrocardiography

State of the Art

Optical Coherent Imaging (OCI) is a non-contact imaging modality utilizing, to a large extent, the physical properties and in particular the coherence properties of light. OCI enables clinical users to better understand tissue viability and healing potentials, to refine risk assessment and optimize treatment decisions, and for better patient management and monitoring. OCI has documented clinical benefits across surgery, burns and advanced wound care, and peripheral vascular applications. Finally, OCI is non-invasive because it involves no physical contact; therefore risk of infection and discomfort are greatly avoided.

OCI modalities can be extended by measuring the response in flow to stimulation. Such approach is called Functional Optical Coherent Imaging (fOCI) and is disclosed in WO/2010/004365.

In PCT/IB2011/051098 an embedded optical coherent imaging device is described which works with a virtual window approach.

Classical microscope designs are used in many medical applications, especially in neuro- and microsurgery, dentistry and ophthalmology. Classical microscopes comprise of illumination and an optical system which interfaces with the surgeon through one or multiple binoculars. The object (Body Area of Interest) is usually magnified by factor 4× to 40×. Some systems further comprise a camera and an external screen on which the result is visualized. Further on, some systems comprise a movement support unit that allows the surgeon to move the microscope without need for his hands, e.g. with a mouthpiece.

Fluorescence imaging is a popular medical diagnostic imaging Modality. The phenomenon of fluorescence is known since 1852. In fluorescence imaging, a fluorescence dye or agent is injected into the blood. The fluorescence dye is excited with a light source of a specific wavelength. The fluorescence dye reacts (absorbs) on the excitation light and emits light at a different (normally longer) wavelength. A detector detects the emitted light (excitation light filtered). Many camera systems implementing fluorescence imaging exist. Some surgical microscopes also have fluorescence imaging implemented. A commonly used fluorescent dye is indocyanine green (ICG), which absorbs at around 800 nm and emits at around 835 nm (see FIG. 6). Other agents exist with different absorption/emission wavelengths. Some agents are used to visualize blood (such as ICG); others can be used to mark specific cells or proteins and are used for example in cancer cell detection; finally, fluorescent markers exist for other types of body flows (e.g. lymphatic flows).

Up to now perfusion imaging devices are limited to a single Modality, sometimes linked to a white-light camera. This often requires users to have multiple devices in the operating room and to change devices during the operation. This is time-consuming, expensive and uses lots of space. Some surgical microscopes have a Fluorescence Imaging Modality but their use is very specialized and optimized for microsurgical cases (such as neurosurgery) only. The use of a classic surgical microscope with Fluorescence is not convenient for operation such as in plastic and reconstructive surgery because the devices are too bulky and the user normally wishes to see a larger area. Surgical Microscopes are also often not used in plastic and reconstructive or general surgery, because the amount of tasks requiring magnification in these fields is limited. Users don't want to use a full surgical microscope for these rare cases.

The virtual window approach is only known for OCI Modalities (see PCT/IB2011/051098), but no device combines multiple Modalities in a single moveable unit.

Having only a single perfusion imaging Modality (Fluorescence or OCI) sometimes has reduced reliability. Two examples shall be given: Fluorescence (ICG) visualizes the concentration of blood in a volume of tissue. If the tissue (e.g. in a thin skin flap) is thinner than the fluorescence signal detection depth, the intensity of the measured fluorescence signal is reduced although perfusion is normal. This is because the volume of the tissue is small with regard to the penetration depth of the fluorescence camera which itself cannot differentiate between specific tissue depths and thicknesses. In such case, however, LDI would show normal perfusion, because the LDI signal is only measured within the top layer of the tissue, thus confirming that the perfusion in the top layer is normal, although the tissue is thin and the fluorescence signal implies week perfusion due to the reduced fluorescence intensity. As another example OCI is very sensitive to movement. A movement artifact can show high perfusion even though the real perfusion is low. This case would be detected using ICG.

Surgeons normally prepare for operations using pre-recorded images taken with CT, X-Ray, MRI or other technologies. During operation they need to review these images. Up to now this is done by having a separate computer and/or presentation wall to look at the images away from the patient. The user needs to move away or turn away from the patient and then manually match the structures he sees on these pre-recorded images to the body and also match data he takes with devices such as perfusion imaging devices with those pre-recorded images.

GENERAL DESCRIPTION OF THE INVENTION

An objective of the invention is to provide a universal medical imaging instrument that combines at least two medical imaging Modalities into a table-like, easy-to-use and intuitive camera for applications inside and/or outside the operating room.

The invention therefore relates to a device as defined in the claims.

FIG. 1 shows an example of a device according to the invention. In this example three Modalities (100) are implemented. Some Modalities share optics (101) while other Modalities have separate optics (102). The Modalities also include processing units (105) for generating their result maps. The result maps are further processed by a general control and processing unit (110). Such unit combines the results from the Modalities as further described in this text. The unit may also control the Modalities and, for example, set parameters based on results from other Modalities. A screen (115) is used to show the results from the Modalities and/or the combination processed by the general processing unit. All Modalities observe a similar Body Area of Interest (130) through the same or nearby apertures/entry points (120). The Body Area of Interest for each Modality can be the same or different while at least a part of it is common among all Modalities. The optical aperture(s) (120) of the Modalities and the Screen (115) to display the results are integrated in a single moveable unit which will be called Device Head. Many of the Modalities require similar optics, mechanics or electronics which can be fully or partially shared. All Modalities share the same screen and the same or nearby aperture/entry point.

Modalities which can be included in such a Device are listed below. The list shall not be limiting and other Modalities not mentioned may also be added to such a Device as well.

Optical Coherent Imaging (OCI) such as Laser Doppler Imaging (LDI) and/or Laser Speckle based Imaging (LSI) to visualize microcirculatory blood flow.

Functional Optical Coherent Imaging (OCI) based technology that measures the change in the microcirculatory blood flow or hemodynamic response to stimulation.

Fluorescence based modality (e.g. with ICG, fluorescein or other fluorophore) to visualize blood flow, nerve activity or any other anatomic or physiological parameter, or to localize specific tissues (e.g. cancer tissue)

3D camera to record the three-dimensional shape of the Body Area of Interest

Spectroscopic imaging

Oxy-/deoxy hemoglobin imaging

Digital microscope (i.e. camera and screen) based modality

Visualization of pre-recorded images such as X-Ray, CT or MRI images, in relation to the current Body Area of Interest.

The results from different Modalities can further be combined to improve the diagnostic value.

to combine the continuous LDI signal with the patency/inflow-outflow information provided by the fluorescence signal;

to map big vessels detected with fluorescence onto perfusion images detected using LSI or LDI;

to optimize parameters for one modality (e.g. sampling frequency of LDI or integration time of LSI) with data determined with another modality;

to assess perfusion at different layers in the tissue;

to show zoomed perfusion image (e.g. subpart of full image) from where a zoomed/microscopic image is shown;

to reduce noise/artifacts and improve reliability by combining results from several modalities that measure the same parameter;

to use several modalities (such as the stereoscopic view from the microscope) to improve curvature correction need on laser Doppler imaging and similar technologies;

to improve cancer detection by combining fluorescence and perfusion imaging modalities;

to improve perforator detection by combining fluorescence imaging with OCI modality;

to improve concentration/speed separation of blood flow by combining fluorescence imaging with LDI or LSI technology;

to use data from several modalities (also from non-coherent technologies) as input to functional OCI for improving the functional mapping;

to detect the direction of flow.

For simplified and hands free operation it is optionally possible to include voice command control. In such case the same device could also allow for audio recording.

DETAILED DESCRIPTION OF THE INVENTION

The invention will be better understood below with a more detailed description illustrated by non-limitative examples.

FIG. 1: Example overview of a Multi-Modality Camera.

Figure 2:
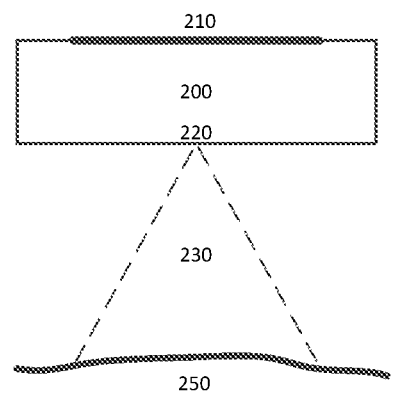

FIG. 2: Illustration of an embodiment of the Device with a screen (210) on the opposite side of the optical sensors (220) all in a single movable unit (200). The sensors capture data from the observed are of the patient (250) through the optics path (230).

Figure 3:
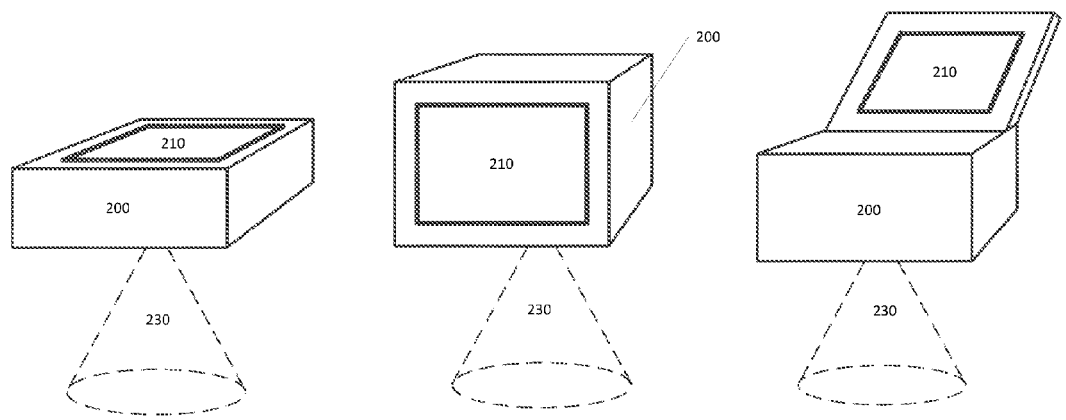

FIG. 3: Examples of embodiments of the Device Head.

Figure 4:
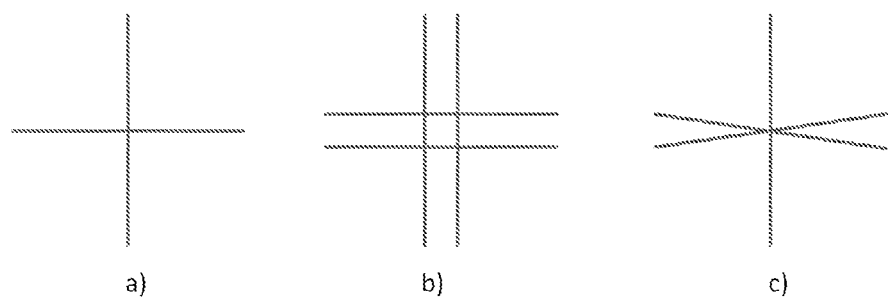

FIG. 4: Example of projection of four line sources to detect the correct Working Distance and camera angle. a) in correct Working Distance, b) not in Distance, c) not parallel to surface.

Figure 5:
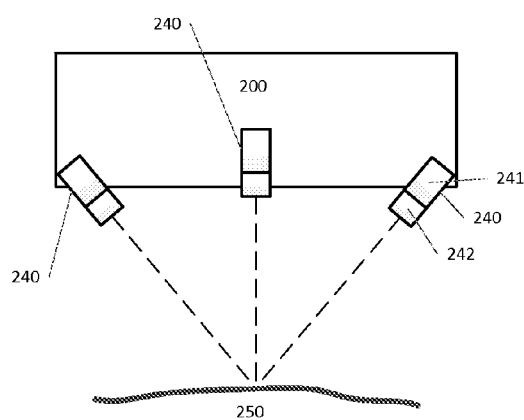

FIG. 5: Example of projection system of three point sources to detect the correct Working Distance.

Figure 6:
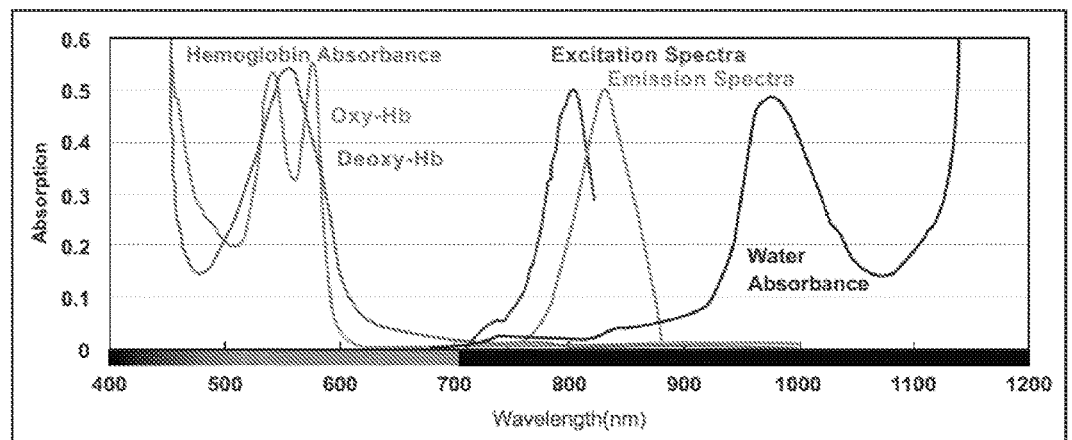

FIG. 6: Excitation and emission spectra of ICG and Hemoglobin, and water absorbance spectra, taken from [Mitsuharu 2009, The Principle of ICG Fluorescence Method].

Figure 7:
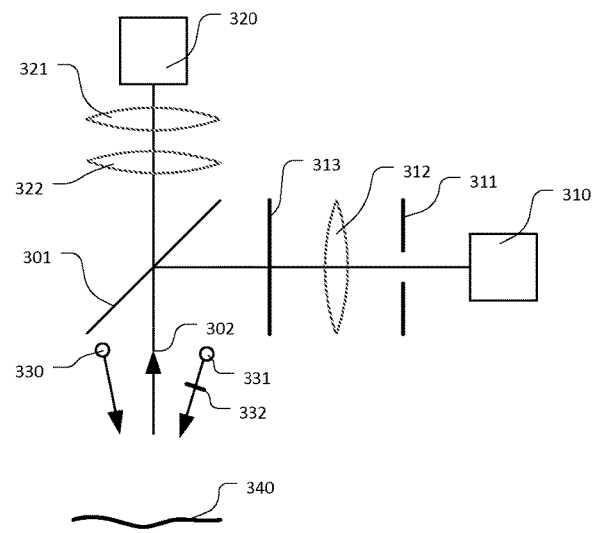

FIG. 7: Embodiment of a Device combining Fluorescence, OCI and Microcopy Modality and sharing a common image sensor for Fluorescence and OCI.

Figure 8:
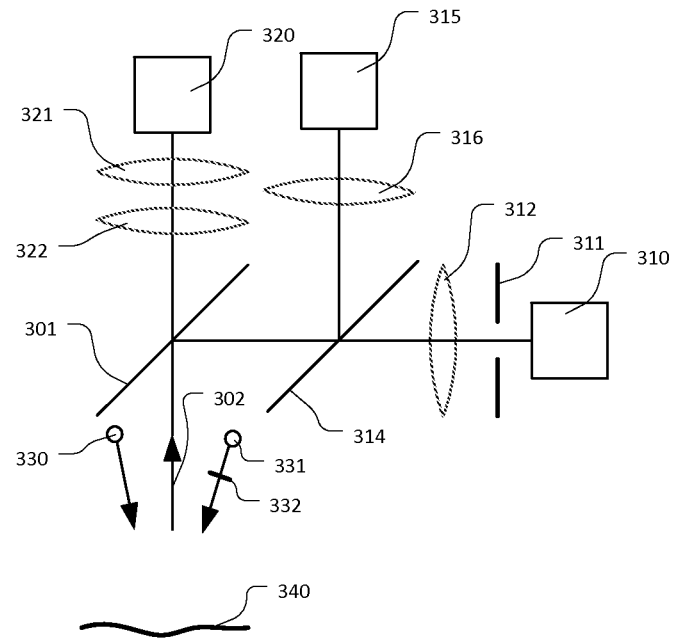

FIG. 8: Embodiment of a Device combining Fluorescence, OCI and Microcopy Modality and sharing a common imaging path.

Figure 9:
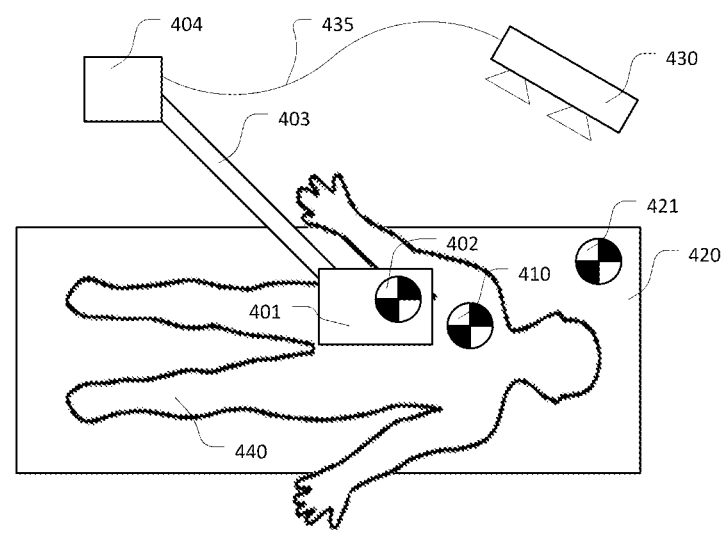

FIG. 9: Example of an embodiment where the position and orientation of the Device Head is detected using a navigation system.

Figure 10:
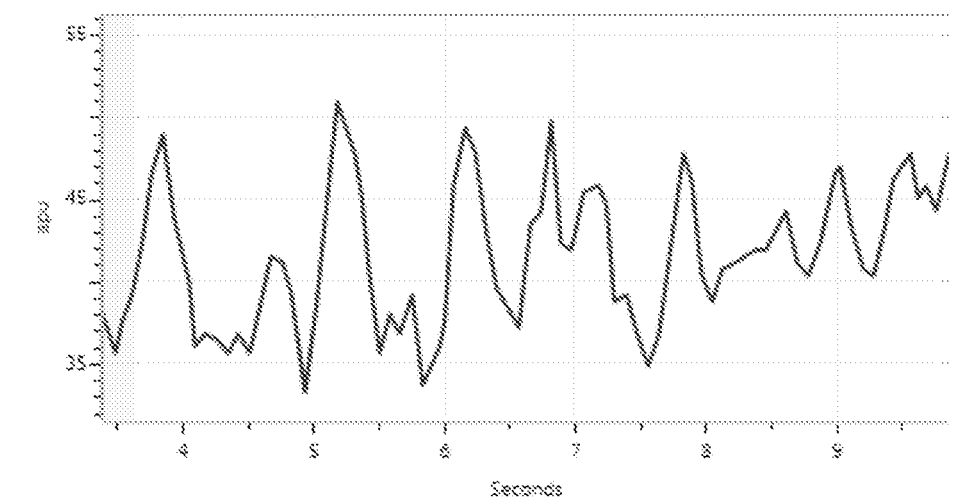

FIG. 10: Plot of the arbitrary perfusion unit (apu) from a region of interest for duration of 6 seconds recorded with a Laser Doppler imaging system.

Figure 11:
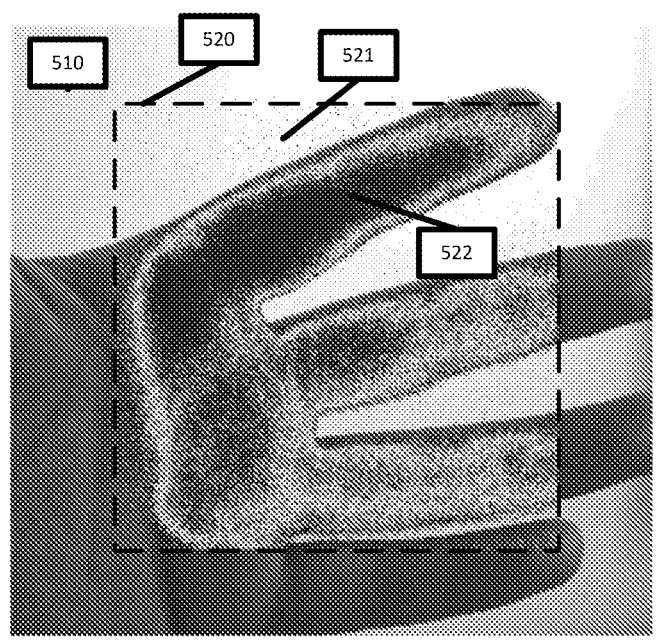

FIG. 11: Example of an overlay of two Modalities. In this example a white-light image is overlaid with an OCI image.

Figure 12:
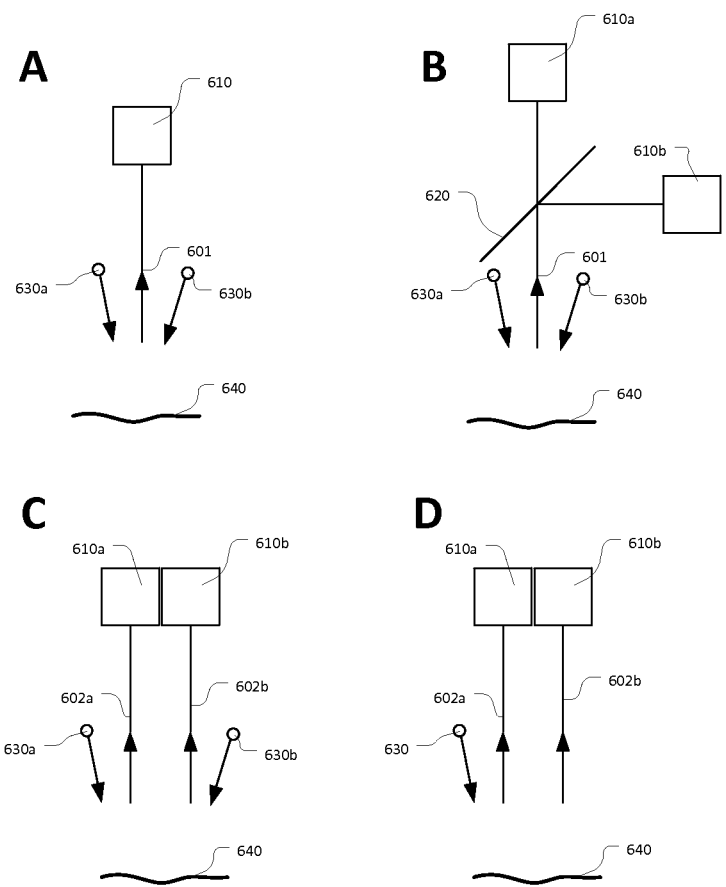

FIG. 12: Example embodiments for Modalities with common optical path.

VIRTUAL WINDOW

One aspect of the invention relates to the easy-to-use of the Device. This usability is facilitated with the combination of the screen (210) and the optical sensors (aperture/entry point for light beam) for all Modalities in a single moveable unit (200). If the user moves the camera unit he automatically also moves the screen for a similar distance. The situation is illustrated in FIG. 2. This single moveable unit shall also be called Device Head in the text. Such Device Head works as a virtual window for the operator who can see the data from the Modalities directly on top of the patient and linked to the position/orientation of the screen in relation to the patient.

In an embodiment the optical system aperture (220) is on the opposite side of the screen. The optical system aperture is the entry point of the optics path for the Modalities into the camera unit. The Modalities image the Body Area of Interest (250) through the optical path (230) and calculate the result images to be shown on the screen (210).

For completeness it shall be mentioned that the screen can also be attached on other positions of the Device Head. Possible positions are the side or any other angle. FIG. 3 shows some examples. In order to allow the user operate with both hands on the patient and because some Modalities require stable data acquisition, in most cases the camera unit is also mounted to a supporting arm. In that case the screen may also be mounted to that arm as long as it is in close proximity of the camera optics and moves together with the camera optics. It is also possible to have multiple screens on the device which display the same or different information.

The processing unit or units for the different modalities can be part of the Device Head or they can be external. In such case the sensor and display data is transferred by cable or with wireless connection means to and from the processing units.

In the preferred way the Device is small such that the user can view the screen and the observed area with direct eye view simultaneously without significantly moving of the head of the user. This would allow the user to see the Body Area of Interest (e.g. surgical site or wound) and the additional information provided by the Multi-Modality Device (e.g. perfusion, fluorescence signal, and/or zoom image) at the same time. For that reason the screen should have a good viewing angle. As a result the user can move its head freely (compared to a classical microscope) which improves ergonomics, and also obsoletes the need to turn the head and try to match something seen on an external screen with a body region in the different line of sight.

Man Machine Interface

The screen can be any type of screen such as an LCD display. The screen resolution, screen responsiveness, contrast and anti-reflection requirement depend on the implemented Modalities (e.g. for microscopy applications a very high-resolution screen is favorable). For some modalities it might also be interesting to visualize 3D or 3D-like images. For example in Digital Microscopy or 3D camera Modality, the data capturing could be done with 3D means such as stereo vision. For such Modalities, the screen could facilitate 3D visualization means with or without requiring the user to wear a special goggle. Many technologies for such 3D screens are known to those skilled in the art. Non-limiting examples are technologies based on polarization, interference, anaglyph, eclipse methods and auto stereoscopy.

The user interaction with the Device, according to this invention, is by touch screen, by physical buttons, by foot pedal, by voice, by external operators or by remote buttons or by any combination of those. The touch screen technology can be resistive, capacitive or any other technologies known to those skilled in the art.

Voice Interface

In an embodiment, the Device can also be fully or partially controlled with voice commands. Such commands can be in the language needed or configured by the device. Commands should be short and may include terms like "Take snapshot", "New Reference", "Change to Microscope", "Change to LDI" or "Zoom in".

In such embodiment the Device further comprises a Microphone and a processing unit which processes the data from the Microphone to understand the command spoken. Methods for voice recognition are known to those skilled in the art. Some or all commands may be read back by the device for confirmation. In such case the Device further comprises a loudspeaker.

Usually all commands which can be executed with the voice interface can be executed with the classical buttons and/or touch screen commands as well.

In addition such Device could be used for audio recording. The recording can be started with a voice command (e.g. "Start Recording") and/or a button/command on the Device or touch screen. Similarly the recording could stop with "Stop Recording" The recorded audio would be saved tagged with the current session information (current patient, operator, etc.) and current timestamp. Such audio recording allows the surgeon to record his activities or observations without need for an addition recording device or notebook and pen.

Optical Coherent Imaging (OCI) Modality

The Optical Coherent Imaging Modality allows visualization of flow properties of the tissue. Usually it measures the microcirculatory blood-flow (perfusion). In such modality a coherent light source such as a Laser is integrated. The wavelength and power depends on the detailed implementation, but the color is usually in the near-infrared range around 800 nm. In Laser Doppler Imaging (LDI) and Laser Speckle Imaging (LSI), the backscattered light is detected by a sensor. Such sensor can be a CMOS, CCD or other reasonable type of image sensor. In an embodiment the sensor is a 2D array of pixels. It is also possible to implement with single pixel or line sensors further comprising scanning means for generating a 2D image.

The signal is then processed by a processing unit. For LDI the processing usually performs a Fourier transform and a moment analysis of the zeros and first moment of the power spectrum. The first moment is proportional to the perfusion. Other algorithms with similar results are known those skilled in the art. For LSI the speckle contrast (spatial and/or temporal) is analyzed. The velocity is non-linearly inverse related to the speckle contrast. The result of the OCI processing is called OCI value and OCI Map. The OCI Map or Maps are usually transformed to images using a colormap (i.e. by assigning a color for each value). The images are then transferred to the display unit.

With an additional control unit it is possible to implement intra-individual relative assessment. In such case the OCI value is not visualized as absolute value, but it is compared to a previously recorded reference value. The image shown on the screen is then calculated relatively to the reference value, which is often indicated in percent.

Function Optical Coherent Imaging Modality (fOCI)

The Functional Optical Coherent Imaging Modality bases on the OCI Modality but further processes the OCI values for functional analysis. In functional analysis the change of the OCI value is analyzed in time and correlated to stimuli. Stimuli can be body-internal stimuli such as heart-beat or breathing, executed stimuli such as finger movement, speech or external stimuli such as application of electrical current or light.

Often the status of the stimuli (stimuli signal) is recorded in parallel with the OCI values. Functional processing is done using Independent Component Extraction (ICE), Regression Analysis or any other statistical method that extracts the statistical significance of a region to a stimuli pattern.

The result can be represented as one or multiple Maps where the Map value relates to the statistical significance (e.g. t-values) of reaction of a zone (hemodynamic response) to the stimuli. The hemodynamic response doesn't match the stimuli completely. Modeling of the hemodynamic response is known to those skilled in the art. As an example when imaging stimuli of the movement of a finger in the motion cortex in the brain, the resulting Map would indicate the zones statistically linked to the finger movement.

The resulting Map are converted to an image using Colormap and transferred to the display unit.

Digital Microscope Modality

The Digital Microscope Modality implements functionality of a microscope or loupe. In such case the user can significantly increase the magnification of a normal white light camera. The user would be able to see structures of sub-millimeter size from the Body Area of Interest on the screen significantly bigger. Magnification factor (from object size to visualization size on screen) could range from 1.5× to 40×. While higher factors are possible as well, they would usually not make sense due to the mechanical vibration properties of the device and the manual precision of the clinical user. The magnifying factor should not limit this invention. In contrary to a classical microscope the user sees the zoomed content on a screen instead of through an ocular. When moving the Device Head, the user automatically also moves the Body Area of Interest. Thus the Digital Microscope behaves like a digital magnifying glass. This facilitates well-known usability from magnifying glass and improves usability compared to classical microscopes.

In an embodiment the Digital Microscope Modality contains a white light image sensor configured such that a body area of interest can be shown with at least 1.5× magnification.

In an embodiment for the Digital Microscope Modality, the device contains lenses and other optical elements arranged to form a zoom objective. The device further comprises an image sensor for detecting the white light image. Such sensor should be a color sensor and can be of CMOS, CCD or any other type. The frame rate should at least be half of the video range, thus at least 12 frames per second. The zoom level preferably is adjustable by the user through input via touch screen, physical buttons, foot switch or other reasonable methods. Zoom levels can be discrete or smooth. Focus is either at a fixed distance or auto-adjusting. Zoom can also fully or partly be done by digital zoom. In an embodiment the optical zoom covers the range of 1× to 5× while a digital zoom adds another lx to 2× or 4× multiplying factor. The zoom factor is preferably shown on the screen. The Device Head is attached to an arm to ensure stability and such that the user can hold off the Device once it is positioned.

According to an embodiment the lenses could be partly or fully implemented using focus tunable lenses which are made from membranes and liquid. Such lens can either be controlled mechanically or by electrical current.

Further magnification can be done by using high-resolution image sensor and performing digital zoom by only using a subsector of full illuminated image sensor and displaying this subsector on the full image output. The quality of the zoomed image can further be improved with filters for contrast/sharpness enhancement. In an embodiment the image sensor contains several million pixels.

According to an embodiment the focus is auto-adjusting. In such case the system adjusts the focus using an adjustable lens system. Detection of the focus distance is done by measuring the distance (e.g. using a light- or ultrasonic based distance sensor), by projecting a known pattern and reading it with the image sensor, by performing a contrast analyzing while adjusting the lens, or by any other means. Auto-focus methods are known to those skilled in the art.

According to an embodiment the Digital Microscope comprises of at least two white light camera systems with similar optical configuration, arranged such that stereographic data can be produced. In such embodiment the signals from both cameras are processed in a processing unit with stereographic algorithms. The result is a fully or partially 3D representation of the observed area.

The screen on the Device can be a classical 2D screen or a 3D screen, 3D glasses or any other 3D visualization method. The user can perform surgery or examine Body Areas of Interest without having their heads fixed to the lens of a classical surgical microscope.

Care should be taken to use camera display and image sensors which reproduce the colors of the Body Area of Interest with good fidelity. In an embodiment this can be supported with good illumination of the Body Area of Interest and with optimized white balance of the image sensor.

Setting the Focal Distance in the Digital Microscopy Modality

In classic microscopes the user looks through an ocular. In such system the optics of the microscope and the optics of the eye form a system and the optics of the eye can partially adjust for focus. In a digital microscope this is not possible.

According to an embodiment the focus depth is large enough to give sharp images from a larger Body Area of interest and/or the focus depth is selectable by the user.

According to an embodiment the user can select the focus point inside the Body Area of Interest. The Digital Microscope comprises an auto-focus system which adjusts its focus such that the image is sharp at the selected point.

According to an embodiment the above selection of the focus point is done manually, for example by touching a point in the image on a touchscreen by the user, or by any other reasonable selection means.

According to an embodiment the above selection of the focus point inside the Body Area of Interest is done automatically based on the position where the primary user looks at. The user's eye is observed using a camera system facing the user's face. Such eye position algorithms are known to those skilled in the art. In clinical environment often several users are looking at the screen. Thus it might be needed to identify the primary user. Such identification can be done based on closest face, longest viewing time, and/or orientation of the GUI relative to the user. In the latter case the primary user is identified as the face which looks at the screen from the side in which the GUI is oriented to him. It is also possible that the user needs to manually select the primary user and the face of such user is further tracked. Such selection could also only be asked if the automated algorithms above for identifying the primary user are not successful.

According to an embodiment the above selection of the focus point is done automatically based on the results from other Modalities. Non-limiting examples are automatically focus on the most/least perfused area or focus on an area which was previously selected from a CT or X-Ray image.

According to an embodiment the above selection of focus point is continuously adjusted based on the movement of the Device Head. The movement is detected as described in a separate section of this invention. The focus point remains the same point on the Body Area of Interest and thus the focus point on the digital image moves by the same distance as the Device Head.

Fluorescence Imaging Modality

The Fluorescence Imaging Modality implements activation and detection of fluorescence.

According to an embodiment the Device comprises a light source which emits light at the desired excitation wavelength of the fluorophore. The desired wavelength depends on the required fluorophore. The light source can be made of a monochromatic light source (such as a Laser) or a light source of any kind with a filter which only allows passing the desired wavelength. It is important that the light source doesn't emit at the emission wavelength of the fluorophore. The light source must illuminate the Body Area of Interest and be strong enough to activate enough fluorophores. The system further comprises a detector (e.g. CCD or CMOS image sensor) and most probably another filter which filters the excitation wavelength and allows passing the emission wavelength.

In an embodiment the detection path is closely aligned with the other optical paths. Using the same path and filtering the emission wavelength using a dichroic mirror can achieve this.

According to another embodiment the Device further comprises a light source with two or more wavelengths and/or detection at two or more emission wavelengths. Measuring with multiple wavelengths allows improved signal-to-noise ratio or subtraction of background noise.

According to another embodiment the Device further comprises a control unit, which allows switching on/off or pulsating the illumination light source at high frequency. The light source state is synchronized with the detection processor allowing for measuring the time-delay of decay of the fluorescence emission. Measurement of the time-delay allows for improved signal-to-noise ratio, subtraction of background noise, and qualification of the fluorophore.

In an embodiment the system is configured for Indocyanine green (ICG) and the illumination wavelength is in the range of 750 to 810 nm, preferably made using Laser light source. The detection frequency is in the range of 830 to 850 nm, preferably around 835 nm. The detection is accomplished using a dichroic mirror which reflects >830 nm to the fluorescence image detector. In another embodiment the image detector is shared with the LDI/LSI detector. In such case all NIR (>780 nm) is transferred to the image sensor. An electrically or mechanically controlled long-pass filter is inserted before the detector for detection of the ICG emission. The same filter is removed for LDI detection. In such embodiment LDI/LSI and Fluorescence Imaging cannot be used at the same time.

According to an embodiment the fluorescence emission signal which is detected by the image sensor is further digitally filtered and transferred to the display unit. Often, the result is colorized and/or overlaid over a normal white-light image of the Body Area of Interest.

According to an embodiment the Device further comprises a processing unit which records and analyzes time-series of the fluorescence emission signal. Such time-series are especially interesting to record the inflow and outflow of the fluorophore into the Body Area of Interest immediately after injection of the fluorophore into the body. This inflow/outflow characteristic can be used to determine flow information in addition to pure concentration information.

Image Mapping Modality

The Image Mapping Modality allows for loading of pre-recorded images from the same patient and showing them on the screen. Such images (Loaded Images) can be pre-recorded with the same Device or they have been recorded with other devices or systems. Non-limiting examples are: LDI images, fluorescence images, X-Ray images, CT images or slices, MRI images or slices, functional images such as fMRI, ultra sound images, PET scans, etc.

In an embodiment the Device detects its position and orientation relative to the patient automatically. See separate chapter in this text. In such case the Loaded Image on the screen is shown such that it corresponds to the body part currently being imaged. For that all Loaded Images should be enhanced with meta-information indicating the body part, location and orientation.

In another embodiment the Loaded Images are automatically or semi-automatically mapped to the Body Area of Interest using a mapping processor. The mapping processor uses photo images or characteristic features linked to the Loaded Image (such as bounders, or markers which are visible on the Loaded Images and are still visible on the patient) for linking the zone in the Body Area of Interest. Such linking could involve detecting marker, borders or image comparison between a camera sensor of the Device and the feature from the Loaded Image. The process can be semi-automated such that the user must navigate to the general body area and/or that he must select mapping features.

In another embodiment the mapping of the Loaded Images is done manually. The Device can still support such process by highlighting markers or features, by showing an overlay of Loaded Image or linked photo image over a current white-light image. Additionally it can fine-tune the mapping once the Device is positioned.

In another embodiment the Loaded Images are independent of the Body Area of Interest currently imaged. Examples are body parameters, medical history record, etc. In such case the Device allows for reviewing of images independently of its position.

Other embodiments are possible. It is also possible to combine aspects from these embodiments in a new solution.

In an embodiment the Device loads the Loaded Images in DICOM format. The device optionally also has access to the PACS (Picture Archiving and Communication System) which is the hospital image data store. In another embodiment the Device can also load images in native file formats or other standard file formats.

Additional Patient or Clinical Information

In an embodiment the Device can show additional information on patient, clinical status and current procedure on the screen. Such information can be loaded from internal store (patient data), from external storage (through hospital information system) or live sources (e.g. patient monitoring systems), from internal sensors or from external sensors.

Internal sensors can be infra-red thermometer, environment thermometer, humidity, etc.

External sensors can be interfaced using any communication means such as cable or wireless connections. Standard interfaces such as Ethernet or hospital interfaces are preferred. External sensor can monitor vital function such as ECG, blood pressure, oxygenation, or any other clinically relevant function.

The sensor values can be shown on the screen, processed or used by the Modalities for optimization.

Same or Similar Optical Axis

In an embodiment the maps/images from all Modalities are obtained, and can be matched such that at least parts of the Body Area of Interest are represented on all maps. In such a case the maps can be transformed such that they can be overlaid.

In an embodiment the Modalities inside the Device Head have at least partially a common optical path. Some examples are given in FIG. 12. If multiple elements of the same type exist, such elements are extended with "a" and "b". A common optical path can be a shared sensing optical path (601) with a shared sensor for multiple Modalities (610) (see Example A), a shared sensing optical path but split using beam splitter (620) to separate sensors (see Example B), or two or more separate sensing optical paths (602) which are fully or almost parallel and have a small offset such that the distortion for the different Modalities is small and the Maps from the Modalities can be transformed such that they can be overlaid (see Example C). A common optical path can also be implemented by sharing light sources (630) between the Modalities (see Example D). The Modalities image at least partially a common Body Area of Interest (640).

In an embodiment the optical setup of the Device Head is such that the optical axis (optical path) looking at the Body Area of Interest is the same or similar between the multiple modalities. However, the numerical aperture and other optical configurations of the individual modalities can be different and independent. In such case the matching of the maps is only dependent of the numeric aperture.

Alternative, if the same optical axis is not possible it is preferred to use parallel axis. In such case the result of the Modalities can be matched by shifting the maps with a constant offset known from the axis offset and the numerical aperture of the Modalities.

Alternatively, if due to mechanical or optical constraints it is not possible to have the same, similar or parallel optical axes, algorithms can be implemented to correct distortion caused by the different axes and to match the results of the multiple Modalities. Such algorithm uses the known optical setup and possibility additional parameters such as the working distance to de-skew the images. Image distortion can also be detected by projecting a known pattern on the Body Area of Interest which is detectable by all relevant Modalities. Such pattern would then be used to adjust the image distortion. Algorithms are known to those skilled in the art.

In an embodiment some elements (e.g. Lasers, beam splitters, lenses, mirrors, prims, image sensors, control and data processing electronic and software, mechanics and motors) of the different Modalities are shared.

Special optical elements such as dichroic mirrors or beam splitters can be used to share the optical path. It is also possible to use optical or mechanical elements (e.g. motorized mirror or electrical controllable filter) to change the path of the optics depending on activated Modalities. In such case some of the Modalities cannot be used at the same time, but switching between the Modalities could be done in short time, up to multiple times per second.

Focus & Working Distance

Depending on the Modalities involved, a variable or fixed working distance might be necessary.

In an embodiment a system is implemented to measure the Working Distance. Such system could be implemented with distance sensors such as Laser based time of flight sensors or ultrasonic based sensors. In some cases it might be interesting to additionally measure the angle of the Device Head relative to the body surface. In such case multiple distance sensors could be used. In an alternative embodiment a projected pattern is used and detected by an image sensor to detect the distance.

If a fixed Working Distance is used, in an embodiment, a Laser alignment system is implemented giving the user immediate feedback whether he is in the right Working Distance. A good alignment system consists of 4 line light sources (such as 4 line Lasers) which have four different aperture positions on the Device Head. Two sources are grouped and aligned such that in Working Distance the two lines match. The two other sources are grouped and aligned such, that in Working Distance the two lines match as well but are orthogonal to the other lines. In the best case the distance between the apertures of each of the two grouped sources on the Device Head is similar. Good colors are red or green. FIG. 4 shows examples of the projection of those line sources. A) is correctly aligned, b) is at wrong Working Distance but parallel to the surface and c) is at correct Working Distance, but not parallel.

An alternative embodiment of the implementation of such fixed Working Distance indication system is shown in FIG. 5 which is already disclosed in PCT/IB2011/051098. At least two collimated light sources (240) consisting of a light source (241) and a collimating optics (242) are placed on different positions of the camera unit (200). These collimated light sources project a small point on the observed surface (250). The small points collide in the focus distance of the camera unit. In the best case the collision point is also in the center of the observed area. With this simple system the user has to bring the camera in such a distance that the two points are projected on the same spot on the observed area and thus only a single projected point is visible. When adding a $3^{rd}$ laser it is also possible to show if the camera is too close or too far from the observed surface with regard to the focal distance.

In an embodiment the fixed Working Distance and variable working distance can be combined. In such case the Device Head operates at a generally fixed working distance, but with some distance tolerance. The focus is adjusted by some Modalities using an auto-focus system with a range of at least the distance tolerance while other Modalities have good enough focus depth not requiring an auto-focus system.

Temperature Measurement/Mapping

In many Modalities it is interesting to know the surface temperature of the Body Area of Interest for interpretation or validation of the results.

In an embodiment the Device contains a contact-less temperature sensor, e.g. an infrared based sensor. Such sensor is pointed to the center of the Body Area of Interest, and can record temperature of the Body Area of Interest either at one single point, at multiple points or over a surface. In case of a flexible Working Distance of the Device, the sensor must be closely aligned with the optical axis or the sensor axis must be adjustable based on the Working Distance. Such adjusting may be done automatically with motorized controls. In an alternative embodiment the Device allows for connection of an external contact based sensor.

In an embodiment a full infrared camera sensor is used and the Body Area of Interest is imaged using this sensor giving a full temperature map of the Body Area of Interest. Such map can be used as an additional Modality or temperature of several points can be extracted and used as meta-data as described in this section.

The sensor values are converted to standard temperature units. The result may be shown on the screen and/or stored with any Modality data as meta-data.

In an embodiment the temperature value is further used to improve the diagnostic information from the Device. In such embodiment a correction database of temperature to perfusion dependencies are stored inside the device. Such dependencies can be further parameterized using patient population information such as gender, age, skin color or disease. The Device then calculates corrected perfusion information in function of the measured temperature and the correction database. The correction database is built from statistical analysis of measurement for each population group.

Combinational use of Elements for Multiple Modalities

In an embodiment the maximum amount of optical, mechanical and electrical elements that are possible to be shared among Modalities are shared. At minimum the Screen or Screens and the Human Machine Interface are shared among all Modalities.

In case of OCI Modality (e.g. LDI or LASCA) the illumination is done using a Laser source usually in the near-infrared wavelength (around 800 nm) and the image sensor detects light at the same wavelength. For Fluorescence imaging often at least one detection wavelength is at the same frequency (e.g. for ICG). Thus it is interesting to use the same image sensor for both LDI and Fluorescence.

According to an embodiment the Device contains Fluorescence (ICG), LDI/LSI and Digital Microscopy Modalities. A schematic drawing of the optical concept is shown in FIG. 7. The Body Area of Interest (340) is illuminated with a coherent Laser source (330). The Laser source needs to be single mode (for LDI/LSI) and have enough power to illuminate the Body Area of Interest with sufficient brightness (several $mW/cm^2$). Illumination wavelength is in the range of 760-810 nm, around 800 nm is preferred. For ICG the required brightness usually is even higher, but single mode is not needed.

Thus it is possible to use the same Laser source as for the LDI/LSI or to change it with a stronger source. Also it is possible to use multiple sources for ICG. Using several sources simultaneously potentially also reduces speckle noise. The backscattered light (302) is split on a beamsplitter (e.g. dichroic mirror) to separate the infrared light from the visible light. The beam splitter reflects wavelength >760-800 nm depending on the Laser wavelength selected and passes the visible light.

For the infrared light the light beam passes a band-pass/long-pass filter (313) which is configured depending on the actual Modality used (LDI vs. ICG). This filter is disabled by mechanical means (such as a motorized movement) or any other reasonable means for LDI/LSI and enabled for Fluorescence. The beam further passes the focus lens system (312) and aperture (311) which is potentially also adjustable depending on Modality. The sequence of focus lens system and aperture can be inversed or even mixed (aperture within the lens system). The image sensor (310) needs to have good quantum efficiency for 800-840 nm wave lengths and ability to be high speed in case of LDI. Technology can be integrating CMOS or CCD sensor while CMOS is preferred.

For the white light camera/Microscope Modality the light beam passes the beam splitter and further passes the zoom lens system (322) which is potentially electronically adjustable and the focus lens system (321) which is fixed or adjustable if an auto focus system is used. The high-resolution color sensor (320) detects the light and produces a color 2D image. The color sensor can be CMOS, CCD or any other reasonable sensor type. Often a white light source (331) is used for uniform illumination of the Body Area of Interest. Such light source can be made of LED or any other reasonable technology for while light illumination. It must be ensured that this light source doesn't emit light in the near infrared (ICG emission) spectrum. This can be facilitated with an addition short-pass filter (332).

According to an embodiment the near infrared sensor (310) is made of an infrared-color sensor which is an image sensor comprising two set of pixels. One set of pixels is band-pass filtered for <=810 nm and the other set is filtered for >830 nm. In such embodiment the long-pass/band-pass filter (313) can be omitted. The image sensor, like a normal color image sensor, returns at least two different images corresponding to the two sets of pixels. The sensor design can be very similar to a color sensor design, except that the wavelength range for the pixels is different from a classical color sensor. The design is known to those skilled in the art.

According to another embodiment the same Device can be implemented with two separate image sensors for LDI/LSI and Fluorescence, see FIG. 8, which allows simultaneous operation of LDI/LSI and ICG. In such embodiment the long-pass filter is replaced with an addition beam-splitter (314). This beam splitter reflects all fluorescence signal (>830 nm in case of 800 nm illumination) and passes all shorter wavelength (or vice versa). The focus lens is implemented with two separate lens systems (316 and 312). The additional image sensor (315) must have good quantum efficiency in the range of 830-840 nm. The required frame rate of this sensor is in the range of a normal video camera.

Combination: Overlay

In an embodiment the results from different Modalities is overlaid on the screen. Examples of such overlay is the overlay of OCI maps over Fluorescence maps or the overlay of OCI or Fluorescence maps over any Image Mapping Modality (e.g. OCI over X-Ray). In any case it is interesting to overlay any Modality over a normal white-light (or Microscopic) image.

An overlay is created by mapping the same point on the Body Area of Interest to the same pixel coordinate. The images are then mixed. Some parts of an image can be set to transparent, e.g. areas where no Fluorescence is detected, or set to semi-transparent. Also, it is possible that not all Modalities cover the same Body Area of Interest. In such case the overlay image either only contains areas where all Modalities cover or the overlay image is only partially overlaid by some Modalities. In such case the area of coverage for each Modality can be visualized.

FIG. 11 shows an example overlay where a perfusion image from OCI modality of a finger is shown. In this example the white-light image (510) with a larger observed area is overlaid with an OCI map (520, border not visible to user). In this example the non- and low-perfused values are set to fully transparent (521) while the other values don't have any transparency (522).

Processing: Differentiate Larger Vessels from Microcirculation

In an embodiment the Device is equipped with Fluorescence (e.g. IGC) and OCI perfusion imaging wherein the two Modalities take simultaneously or short time interval sequential maps from at least partially a common Body Area of Interest. The Device further comprises a processing unit which compares the data from both Modalities.

The Fluorescence Modality basically measures the concentration of the Fluorophore, and because the Fluorophore such as ICG is bound to the blood, it shows the concentration of blood. Its value is basically independently of the speed of blood. OCI perfusion imaging visualizes the perfusion which is proportional to speed. OCI has a maximum speed that it can detect. Depending on technology the faster-than-maximum-speeds are detected with the maximum speed or even with a lower value (anti-aliasing effect).

The comparison between Fluorescence and OCI Modality data can be used to differentiate microcirculatory Perfusion from larger (and thus faster) vessels. While both technologies respond on the microcirculatory flow, only Fluorescence responds on the larger vessels. An example of such comparison is a simple weighted subtraction of the OCI map from Fluorescence map. The OCI map can be perfusion or concentration map.

In order to perform such comparison also the penetration depth must be considered. If the penetration depth of the two Modalities is significantly different, the comparison can also be used to differentiate contribution of blood flow in different depth of the tissue.

In another embodiment the Fluorescence image is first recorded. The Fluorescence image is then overlaid to real-time OCI images. Potentially the Fluorescence is further filtered to highlight the large vessels only. This can be done using the procedures described above or by taking a distinct image during inflow of the Fluorophore. In such case the image shown to the user contains the large vessels detected using Fluorescence Modality and the real-time microcirculatory perfusion using OCI Modality. The overlay images are matched such that if the user moves the Camera Head the large vessels move as well in order to still align with the OCI images. Such alignment solutions are discussed elsewhere in this text but may include markers visible from both Modalities, and/or position/orientation information of the Device Head.

Processing: Penetration Depth

Different Modalities can have different penetration depth. For example often Fluorescence Modality has a deeper penetration depth into the skin than OCI.

Knowing the penetration depth of the Modalities a comparison of the results from the Modalities can help to evaluate perfusion in different levels of the skin. Thus in an embodiment the combination of the data from Modalities with different penetration depth is used to assess the perfusion at different levels inside the skin and sub-cutaneous tissue.

As example ICG-based fluorescence perfusion imaging normally has deeper penetration into the skin than OCI, and can therefore also help evaluate perfusion in deeper and sub-cutaneous structures, whereas OCI is limited to the top layers of the skin. In well perfused, but thin skin flap areas, the ICG-based perfusion signal seems week, because the volume of blood is small. At the same time the OCI-based perfusion signal is strong. Thus, purely looking at ICG would lead to the wrong conclusion that this flap area is not viable. The combination of both modalities therefore results in a higher clinical performance than when using the individual Modalities alone.

Processing: Improve Reliability of Modalities

Having several Modalities implemented in the same Device which measures the same or similar parameter (e.g. ICG and LDI to assess perfusion) can be combined to improve the reliability of the measurement.

In an embodiment Fluorescence Modality (e.g. ICG) and OCI Modality (such as LDI or LSI) are combined. The two Modalities observe a common Body Area of Interest. The maps produced by those Modalities are processed by a processing unit. The processing unit compares the maps. Areas where the two Modalities match with their result (e.g. higher/lower perfusion than average or absolute value) have increased reliability while areas where the results differ have decreased reliability. The processing unit creates an addition map with the reliability information for each area. This map can have the same resolution as the maps from the Modalities or a reduced resolution.

In an embodiment the above mentioned combination is also used to detect movement of the Device Head. While movement of the Device Head significantly increases the measured perfusion with OCI Modality, the Fluorescence signal is not increased. A processing unit analyzes the data in a time-series and detects increase in perfusion from OCI Modality without significant increase of the Fluorescence signal. Such case is marked as unreliable.

In an embodiment the above mentioned processing unit additionally produces a new perfusion map with combined information from both modalities.

In order to differentiate between large vessels and unreliable data, time series of data can be analyzed. Especially the phase of inflow of the Fluorophore can help to differentiate as the flow in the large vessels is viewable before the flow in the microcirculation.

Processing: Heart-beat

Another object of this invention is the connection of external monitoring devices with the Device. In an embodiment a Device equipped with OCI Modality is further connected to a monitoring device that supplies real-time ECG, heart-beat or pulse information. This information is used to analyze perfusion images taken with the OCI modality. The OCI modality takes several images with >4 Hz frame rate. When comparing the dynamics of the OCI modality to the heart beat information, the quality of the OCI map can be improved. Corresponding peaks in the perfusion to the heart beat can be removed or identified. Any pulsation lag can be analyzed as well. Additionally all dynamic peaks which don't correspond to the heart beat (especially with different frequency) can be identified as well. Such peaks would be introduced by other physiological factors or are artifacts (such as due to movement). Thus the connected monitoring device can improve the signal quality and reduce or identify noise. An example is given in FIG. 10 where the arbitrary perfusion unit (apu) from a region of interest for duration of 6 seconds recorded with a Laser Doppler imaging system is plotted. As visible on this plot peaks are visible with 1 second interval which mostly relates to the heart beat. But not all peaks are in a constant frequency and necessarily correlate to the heart beat. Having addition external heart beat monitoring synchronized with the OCI modality data would allow for improved analysis of the measured signal. Some peaks could be assigned to heart beat while others are assigned to other or unknown source. Such analysis could also be achieved with independent component extraction ICE.

In an embodiment where the OCI Modality is implemented with scanning methods and the acquisition of a single frame takes almost a second or more, the heart beat signal can be used to remove effects from the heart beat during scanning. In such case each pixel value of the scanning OCI system could be weighted based on the phase of the heart-beat. To understand the general heart-beat related pulsation of the OCI signal, the scanning system could measure full cycles of the heart-beat at a few points in the map. The correlation of the pulsation of the OCI signal at those points with the external heart-beat signal is used to calculate the pulsation related weight to be used.

Processing: Cancer Detection with Fluorescence and OCI Modality

Another aspect of this innovation is improved cancer detection with combination of Fluorescence imaging and perfusion imaging. Specific Fluorescence agents which can be used to detect cancer cells are known to those skilled in the art. Those agents attach to specific proteins or other molecules which are found in specific cancer cells. While some finalized agents exist, many are still being developed. It is also known that some types of cancer show hyper or hypo perfusion thus the cancer show increased or decreased perfusion compared to normal tissue.

In an embodiment Fluorescence Imaging and OCI Modality are combined. The analysis of both modalities can increase reliability of the detection. For example a cancer type known for hyper perfusion and binding with a specific Fluorophore can be detected more reliably if both Modalities show the expected response (increased perfusion and Fluorescence response). Also, it is possible to further differentiate the cancer type if a Fluorophore binds to different types and the additional information of hyper/hypo perfusion differentiate the cancer type. In such embodiment a processing unit analyzes the maps from both Modalities and looks for common or different (relative) data in the maps.

The above mentioned methods also work for other type of tissue detection which base on specific Fluorescence agents and which can further be identified/differentiated using perfusion information.

Position and Orientation of Device Head Relative to Patient

In some embodiment it might be necessary to detect the position and/or orientation of the Virtual Window relative to the patient body. Such detection of the body can be facilitated with several methods.

In an embodiment Optical Marker are affixed to the patient body in the area of the zone of interest. Such markers are then detected using sensors in the Device Head. Such sensor could be any camera sensor from any imaging Modality present in the Device or a specific sensor such as a dedicated camera sensor. The position of the marker relative to the camera head is calculated using the information of the sensor, the optical configuration and the known or measured working distance. It is also possible to use multiple sensors and/or to process stereo vision for working distance independent position calculation.

In another embodiment the Device Head is equipped with Optical Markers (402) which can be detected by an external 3D stereo camera of a navigation system (430). Similar Optical Markers (410) are mounted to the body of the patient (440) and/or to any other equipment which has a known position relative to the patient, such as the operating room table (420, marker 421). The navigation (stereotactical) system calculates the position of all Optical Markers and sends the absolute and/or relative position information to the Device. The information is sent by any means such as cable (435) or wireless communication. Such a system is shown in FIG. 9. In this example the Device Head (401) is mounted to an arm (403) and a stand (404). The arm and stand are not required for the operation of the navigation system. In some setups not all Optical Marker would be visible by a single 3D stereo camera. In such case multiple 3D stereo cameras can be used or redundant marker can be affixed. Stereotactical systems are known to those skilled in the art.

In another embodiment the Device Head is mounted to an arm and stand which are equipped with joint sensors or other sensors facilitating the calculation of the Device Head relative to the stand base. The stand base can be fixed to the ground, e.g. using breaks on its wheel. The user uses the Device Head to point to (image) several points on the patient body. The camera stores the optical configuration, the relative position of the Device Head to the stand and possibly the working distance. Based on this information and as long as the camera stand is not moved (or the movement is known), the Device Head is "calibrated" to be able to calculate the position of the Device Head relative to the patient.

Other embodiments are possible. It is also possible to combine aspects from these embodiments in a new solution.

Usually the Device uses the optical configuration of the Modalities as additional information to calculate the absolute imaging zone on the body of the patient.

Such position detection is necessary for Image Mapping modality, but it is also useful for other modalities in which the position information can be used to store location information for each recording and such recording could be combined in post-processing using the location information.

In an embodiment the position and orientation information is saved together with captured images and videos.

Relative Device Head Movement Information

Instead of calculating the position of the Device Head relative to the patient, it is sufficient in some Modalities and applications to detect the movement of the Device Head only. In such case the position information is limited to the position and orientation of the Device Head relative to a virtual coordinate frame. The virtual coordinate frame is different for each session of the device and may fully, partially or not at all be linked to the coordinate frame of the patient.

In an embodiment such detection could be facilitated with a combination of motion sensors (acceleration sensors, gyroscopes) and/or joint angle sensors. A processing unit fuses the sensor data and calculates the movement of the Device Head.

Image Stitching

Position and orientation information of the camera, independent if absolute or relative, can be used to stitch captured data together. Captured data can be any captured image or video from any Modality.

Stitching the images together is done by a processing unit which uses the position and orientation information of each captured data/frame to align them on a big image. Such processing can be done in the Device or with external software utilizing the position/orientation information. The algorithms needed include image distortion and transformation and are known to those skilled in the art.

Knowing the general body shapes the positioned image can further be mapped to a 3D model of the body.

Data Capturing

In an embodiment it is possible to capture data from several Modalities at the same time or within a very short time in sequence. Such capturing can be done with single snapshots or full video recordings. Additional information such as the position and orientation of the Device Head, working distance and optical configurations, or other sensor values can be stored as metadata. Post processing allows the matching of the data of the different modalities.

The results of the different Modalities are preferably stored in a single file, but some or all Modalities can also be stored in separate files. While custom file formats are possible, in an embodiment, the results are stored in DICOM file format. DICOM is a widely accepted, extendable file format in medical field.

Functionality Available When Needed

In some clinical and surgical settings, the information provided by one of the mentioned imaging Modalities is sufficient. However, in other settings, at least two of the mentioned imaging Modalities are required. Having them integrated into a single device allows the user to turn these Modalities on when needed, without having to move around equipment.

Usage Based Management and Billing

As each Modality at least partially involves digital processing, detailed Device usage statistics can be obtained and recorded. This enables business and billing models that are based on the usage of the Device and its Modalities. Among the parameters that can be recorded are the used Modalities, the time of use, amount of images and videos recorded, or information related to the specific of patient or operator, or the amount of analysis performed by algorithms of the system. A typical work-flow would look as follows:

1. Start or resume device
2. Enter patient information and optionally select operator
3. Choose primary Modality and start the imaging session
4. Operate the Modality, optionally record information obtained from the Modality
5. Optionally add other Modalities
6. Finalized the imaging session In an embodiment the usage information is recorded by the Device and transferred to a billing center at regular interval (e.g. by means of secure electronic transmission). The billing center then invoices the usage based on a pre-defined price plan.

In an alternative embodiment the users prepays credits for using the Device. Credits can be specific to a Modality or generic. In case of generic credits each Modality might require a different amount of credit for its usage.

The two embodiments mentioned above may also be combined. Credits could also be given when bundled with consumables (e.g. implant or ICG). This could be done by scanning a barcode (e.g. with camera from the Device or with specific barcode reader) given with the implant, by means of near-field communication such as RFID, or any other transfer of authorization code. Such authorization code could only be scanned once. This limitation could be implemented by having a database on the system which stores the already used codes.

Implementation of such usage-based billing is optional and may also be combined with capital equipment based business modes.

It is also possible to enable/disable Modalities based on licensing.

The invention claimed is:

1. A perfusion assessment multi-modality optical medical device comprising:
    a coherent light source for illuminating a body area of interest;
    an optical coherent imaging (OCI) image sensor that detects fluctuations of backscattered light near the illumination wavelength from at least part of said illuminated body area of interest;
    a fluorescence image sensor to detect a fluorescence signal at a wavelength different from the illumination wavelength from at least part of said illuminated body area interest;
    a screen, the coherent light source, the OCI image sensor, the fluorescence image sensor, and the screen are included in a single movable unit, said OCI image sensor, and said fluorescence image sensor, at least partially, use a common optical path; and
    a processing unit coupled to the OCI image sensor and the fluorescence image sensor for comparing the blood flow or perfusion information in the OCI image and in the fluorescence image to differentiate microcirculatory blood perfusion from larger vessels with the blood flow being faster in the larger vessels and wherein the results of the comparison are displayed on the screen.

2. The device according to claim 1, wherein said OCI image sensor and said fluorescence image sensor are a single image sensor.

3. The device according to claim 1, further including a white light image sensor and an optical system configured to image the body area of interest and wherein the white light image sensor is configured such that a body area of interest can be shown with at least 1.5×magnification.

4. The device according to claim 1, further comprising detecting means for the position and orientation of the device head in relation to a patient.

5. The device according to claim 4, wherein the processing unit renders stored images and/or metadata related to the currently visualized body area.

6. The device according to claim 1, wherein the processing unit is used to generate an overlay image from the OCI image information and fluorescence image information.

7. The device according to claim 3, further comprising an auto-focus system for the white light image wherein the focus point is automatically detected by locating the point on the screen which is focused by the user's eye.

8. The device according to claim 1 wherein coherent light source generates a wavelength of 760-810 nm.

9. A perfusion assessment multi-modality optical medical device comprising:
- a coherent light source for illuminating a body area of interest;
- an optical coherent imaging (OCI) image sensor that detects fluctuations of backscattered light near the illumination wavelength from at least part of said illuminated body area of interest;
- a fluorescence image sensor to detect a fluorescence signal at a wavelength different from the illumination wavelength from at least part of said illuminated body area interest, said OCI image sensor, and said fluorescence image sensor, at least partially, use a common optical path;
- a screen; and
- a processing unit coupled to the OCI image sensor and the fluorescence image sensor for comparing the blood flow information in the OCI image and in the fluorescence image to differentiate the contribution of blood flow in different depths within the body area and wherein the results of the comparison are displayed on the screen.

10. The device according to claim 9, wherein said OCI image sensor and said fluorescence image sensor are a single image sensor.

11. The device according to claim 9, further including a white light image sensor and an optical system configured to image the body area of interest.

12. The device according to claim 9 wherein coherent light source generates a wavelength of 760-810 nm.

13. A perfusion assessment multi-modality optical medical device comprising:
- a coherent light source for illuminating a body area of interest;
- an optical coherent imaging (OCI) image sensor that detects fluctuations of backscattered light near the illumination wavelength from at least part of said illuminated body area of interest;
- a fluorescence image sensor to detect a fluorescence signal at wavelength different from the illumination wavelength from at least part of said illuminated body area interest, said OCI image sensor, and said fluorescence image sensor, at least partially, use a common optical path;
- a screen; and
- a processing unit coupled to the OCI image sensor and the fluorescence image sensor for comparing the blood flow or perfusion information in the OCI image and in the fluorescence image to determine the reliability of the measurements, wherein when the results of the comparison are similar, the measurements are considered more reliable than when the results are different and for generating and displaying on the screen a reliability map.

14. The device according to claim 13, wherein said OCI image sensor and said fluorescence image sensor are a single image sensor.

15. The device according to claim 13, further including a white light image sensor and an optical system configured to image the body area of interest.

16. The device according to claim 1 wherein coherent light source generates a wavelength of 760-810 nm.

* * * * *